United States Patent [19]

Lenaghan

[11] 4,405,326
[45] Sep. 20, 1983

[54] CATAMENIAL BANDAGE

[76] Inventor: Arlene R. Lenaghan, 674 Rudgate, Bloomfield Hills, Mich. 48013

[21] Appl. No.: 269,360

[22] Filed: Jun. 1, 1981

[51] Int. Cl.³ .................................................. A61F 13/18
[52] U.S. Cl. .................................... 604/385; 604/393; 604/397
[58] Field of Search ............... 128/284, 286, 287, 288, 128/290 R, 290 W, 296; 604/358, 385, 393, 397, 398

[56] References Cited

U.S. PATENT DOCUMENTS

| 2,468,445 | 4/1949 | Hurst | 128/287 |
| 2,506,238 | 5/1950 | Rowe | 128/287 |
| 2,721,554 | 10/1955 | Joa | 128/290 R |
| 2,815,027 | 12/1957 | Makela | 128/290 R |
| 3,070,096 | 12/1962 | Weitzman | 128/287 |
| 3,369,545 | 2/1968 | Wanberg | 128/287 |

Primary Examiner—C. Fred Rosenbaum
Assistant Examiner—Sherri Vinyard
Attorney, Agent, or Firm—Barnes, Kisselle, Raisch, Choate, Whittemore & Hulbert

[57] ABSTRACT

A catamenial bandage pad having a soft, curved-sided shell with an elongate transverse plate, made of a molded plastic material which is form-retaining and has a characteristic to return to its original shape even though momentarily deformed by body position. The shell is filled with an absorbent material and enveloped in a retaining gauze. A self-wrapping end retainer holds a folded used pad in a double back position.

1 Claim, 13 Drawing Figures

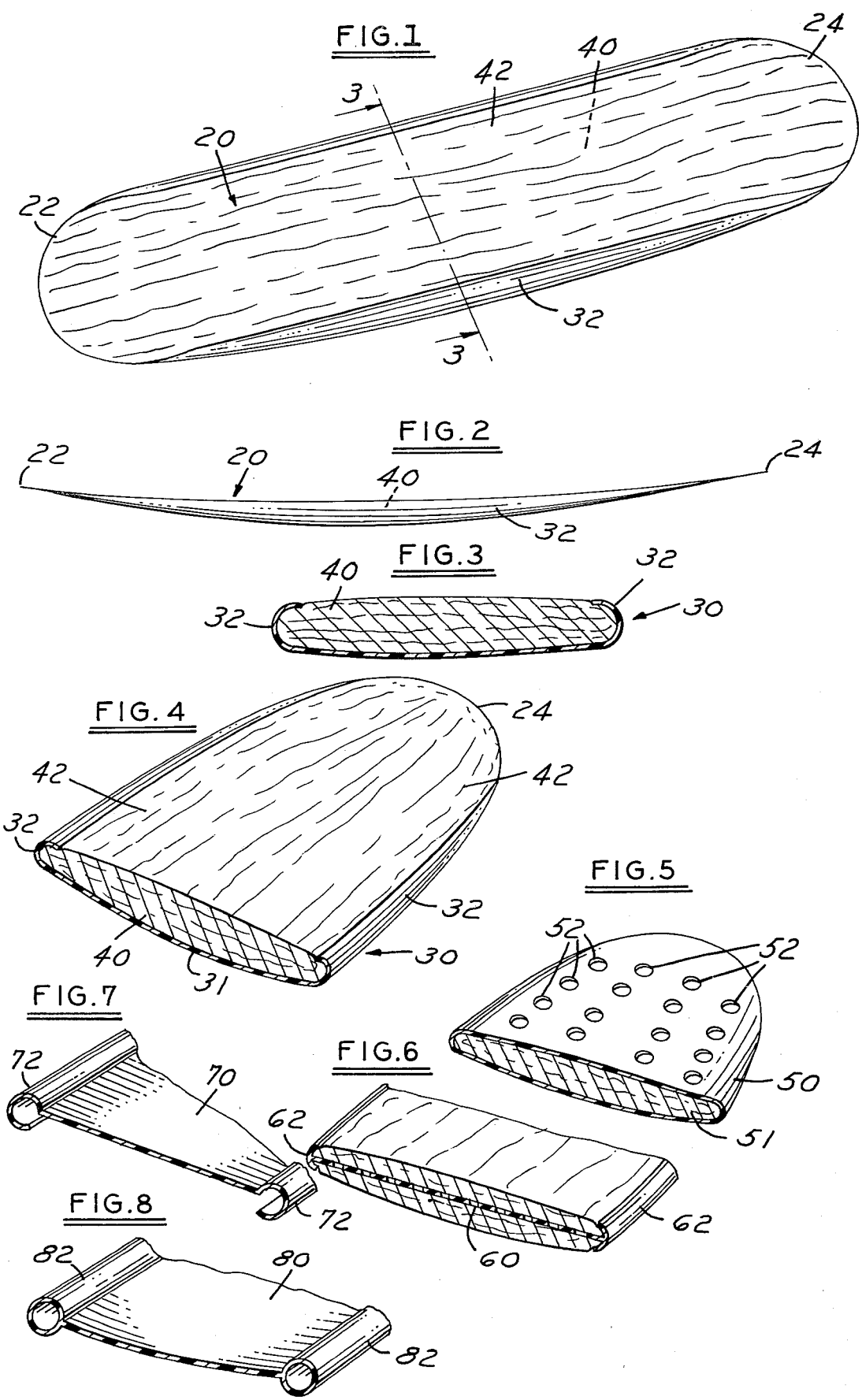

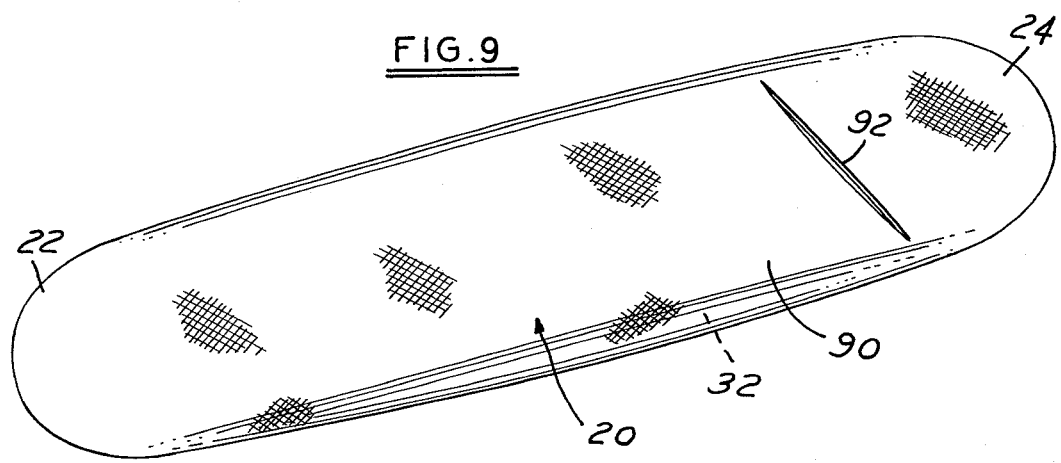
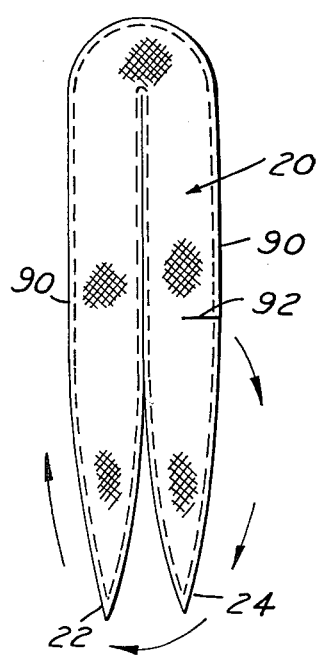
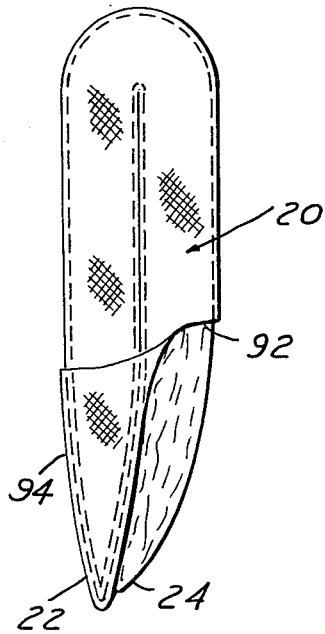
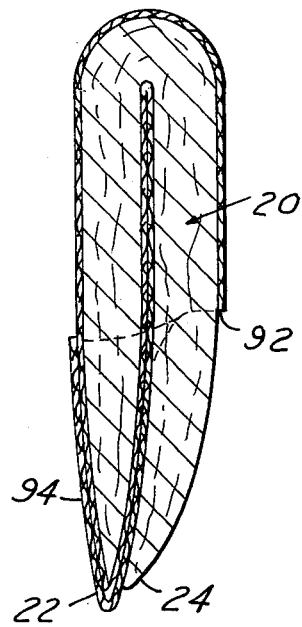
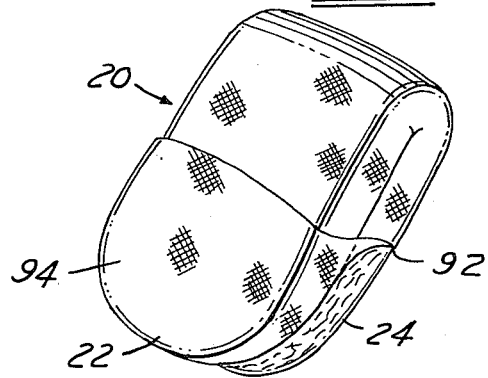

CATAMENIAL BANDAGE

REFERENCE TO RELATED APPLICATION

Reference is made to my copending application entitled "Catamenial Bandage", Ser. No. 269,361, filed June 1, 1981.

FIELD OF INVENTION

The design and manufacture of sanitary pads for use by women in the menstrual period.

BACKGROUND OF THE INVENTION

In recent months, the use of the tampon type menstrual device has been under investigation due to a toxic syndrome which has affected certain women using this type of device. This has caused a return to the more conventional sanitary pad but has resulted also in the focus of attention to the inadequacies of the usual elongate pad. These inadequacies include discomfort in use, deformation or roping which reduces the effectiveness of the absorbency, inability to adapt to variations in flow, and a resulting lack of confidence in the pad itself.

The present invention is directed to an improved type of sanitary pad which provides a more comfortable device which holds its shape and provides the necessary protection without loss of absorbency and which adapts readily to varying conditions.

Other objects and features of the invention will be apparent in the following description and claims in which the invention is described together with the manner of making and using the invention directed to persons skilled in the art.

BRIEF DESCRIPTION OF THE DRAWINGS

Drawings accompany the disclosure and the various views thereof may be briefly described as:

FIG. 1, a perspective view of the improved sanitary pad.

FIG. 2, a side view of the pad shown in FIG. 1.

FIG. 3, a sectional view on line 3—3 of FIG. 1.

FIG. 4, a perspective view of one end of the device.

FIG. 5, a view of a modified construction using a cylindrical form.

FIG. 6, a further modification of a reinforcement element.

FIG. 7, another species of pad construction.

FIG. 8, still another species of a reinforcing element.

FIG. 9, a view of a covered pad with a disposal slit for folding.

FIG. 10, a view of a first step in disposal folding.

FIG. 11, a view of a second step in the disposal folding.

FIG. 12, a vertical view of the device in FIG. 11.

FIG. 13, a perspective view of the folded device.

DETAILED DESCRIPTION OF THE INVENTION

Reference is made to certain patents selected in a search as most pertinent to the invention described and claimed herein. These are:

Wrap-Up Concept

U.S. Pat. No. 3,604,423—Sept. 14, 1971—Fraser
U.S. Pat. No. 3,973,567—Aug. 10, 1976—Srinivasan Transverse Reinforcement U.S. Pat. No. 2,964,041—Dec. 13, 1960—Ashton
U.S. Pat. No. 3,570,493—Mar. 16, 1971—Olsson Edge Formation U.S. Pat. No. 3,575,174—Apr. 20, 1971—Mogor
U.S. Pat. No. 4,072,151—Feb. 7, 1978—Levine As shown in FIGS. 1 and 2, the sanitary pad 20 is elongate in form, rounded at the ends 22, 24, and curved from end to end. The ends are gradually tapered in thickness from the center, the thickest portion being in the center as shown in the sectional views, FIGS. 3 and 4.

The pad 20 is made up of a molded shell 30 formed of a soft, molded plastic similar to that used in packaging today having a soft velvety feel and readily deformable yet having a form retaining characteristic. The shell has a plate portion 31 which is curved around the sides at 32, this curving decreasing as the ends are approached until at the ends the shell is essentially flat with no rim. The shell 30 is filled with an absorbent material 40 retained by a gauze or fabric cover sheet 42.

In FIG. 5, a modified structure is illustrated having a flat cylindrical shape 50 enclosed to retain the absorbent material 51 but provided with a plurality of openings 52 to conduct menstrual discharge to the absorbent material. Otherwise, the shape of the device is similar to that shown in FIGS. 1 to 4.

FIG. 6 shows a modified structure with a flat plate sheet 60 of soft plastic reinforcement centrally of the pad with curved sides 62. The sheet 60 can be perforated to utilize the filler material on both sides. The plate 60 interconnects with curved sides midway between the lateral edges of said sides.

In FIG. 7, a modified reinforcement element is shown with a central plate 70 and reverse-curved, open tubular sides 72 which ensmall towards the ends to a flat end construction.

In FIG. 8, a device is shown with a central plate 80 and closed tubular sides 82 rounded on the outer surfaces and again tapering to the flat ends as in FIGS. 1 to 4.

The devices shown in FIGS. 1 to 8 would be retained on the body in conventional ways by garter belts, special panties or other common devices presently used for these purposes.

In FIGS. 9 to 13, there is illustrated a means for wrapping the used pads. Each of the previously described structures would have a gauze wrap around both sides as is presently the case with these devices.

In FIG. 9, the outer wrap is shown at 90. This wrap 90 has a transverse slit 92 adjacent to but spaced from one end on the outer side of the pad. After use, the pad is folded with the inner side folded on itself as shown in FIG. 10. The gauze 90 which is stretchable is pulled or peeled away at the slit 92 and stretched back over the end 22 at 94 to envelope the end and hold the two ends 22 and 24 together. FIG. 11 shows this enveloping. FIG. 12 is a section which also illustrates the fold and fastening by the stretching of one end over the other. FIG. 13 shows the wrapped device in perspective.

Thus, the soiled side of the pad can be enclosed in the folded pad and retained as indicated. This will eliminate the need for wrapping the used pad.

In use the plastic shell with the transverse elongate sheet and curved side walls of the shell will retain shape and resist roping, i.e., bunching up transversely while providing comfort at the sides and a resilient "give" in various movements of the body. Thus, the pad will retain its full absorbent capacity throughout its use and afford efficient protection.

What I claim is:

1. A catamenial bandage pad which comprises:
  (a) a molded shell of soft, resilient, form-retaining material having a plate portion elongate in form extending transversely and longitudinally of the pad, said shell having curved sides extending in a direction perpendicular to the plate portion and narrowing from the longitudinal center of the pad to the ends, and
  (b) an absorbent material extending over said plate between said curved sides,
  (c) said shell and absorbent material being enveloped in a gauze covering, said covering having a transverse slit on the outside of said pad adjacent one end, said covering between said slit and the end to which it is adjacent being peelable away and stretchable over the other end of said pad when folded to said first end to retain said pad in folded condition.

* * * * *